(12) United States Patent
Hermann et al.

(10) Patent No.: US 6,682,915 B2
(45) Date of Patent: Jan. 27, 2004

(54) PROCESS FOR THE FERMENTATIVE PREPARATION OF D-PANTOTHENIC ACID AND/OR ITS SALTS

(75) Inventors: Thomas Hermann, Bielefeld (DE); Achim Marx, Halle (DE); Walter Pfefferle, Halle (DE); Mechthild Rieping, Bielefeld (DE)

(73) Assignee: Degussa AG, Duesseldorf (DE)

( * ) Notice: Subject to any disclaimer, the term of this patent is extended or adjusted under 35 U.S.C. 154(b) by 13 days.

(21) Appl. No.: 10/052,388

(22) Filed: Jan. 23, 2002

(65) Prior Publication Data

US 2002/0137149 A1 Sep. 26, 2002

(30) Foreign Application Priority Data

Feb. 13, 2001 (DE) .......................................... 101 06 461

(51) Int. Cl.$^7$ .............................. C12P 7/46; C12N 9/10; C12N 1/10; C12N 15/00; C12N 21/06; C07H 21/04
(52) U.S. Cl. ................. 435/146; 435/193; 435/252.33; 435/320.1; 435/69.1; 536/32.2; 426/7
(58) Field of Search ................................ 435/146, 193, 435/252.33, 320.1, 69.1; 536/23.2; 426/7

(56) References Cited

U.S. PATENT DOCUMENTS 5,518,906 A    5/1996    Hikichi et al.

FOREIGN PATENT DOCUMENTS

| EP | 0 493 060 | 7/1992 |
|---|---|---|
| EP | 1 001 027 | 5/2000 |
| EP | 1 050 219 | 11/2000 |
| GB | 2 130 216 | 5/1984 |
| WO | WO 96/33283 | 10/1996 |
| WO | WO 01/00843 | 1/2001 |
| WO | WO 02/061108 | 8/2002 |
| WO | WO 02/072838 | 9/2002 |
| WO | WO 02/072840 | 9/2002 |

OTHER PUBLICATIONS

M. D. Plamann, et al., Nucleic Acids Research, vol. 11, No. 7, pp. 2065–2075, XP–002232264, "Complete Nucleotide Sequence of the *E. coli glyA* Gene", Apr. 11, 1983.

N. Monschau, et al., Applied and Environmental Microbiology, vol. 64, No. 11, pp. 4283–4290, XP–000857901, "Threonine Aldolase Overexpression Plus Threonine Supplementation Enhanced Riboflavin Production in *Ashbya Gossypii*", Nov. 1998.

*Primary Examiner*—Rebecca E. Prouty
*Assistant Examiner*—Sheridan L Swope
(74) *Attorney, Agent, or Firm*—Oblon, Spivak, McClelland, Maier & Neustadt, P.C.

(57) ABSTRACT

A method for the fermentative preparation of D-pantothenic acid and/or its salts or feedstuff additives containing these. Said method comprising, fermentation of *Escherichia coli* microorganisms wherein the nucleotide sequence(s) coding the glyA gene is overexpressed.

10 Claims, 2 Drawing Sheets

PROCESS FOR THE FERMENTATIVE PREPARATION OF D-PANTOTHENIC ACID AND/OR ITS SALTS

This application claims the benefit of priority to Germany 101 06 461.6 filed Feb. 13, 2001.

BACKGROUND OF THE INVENTION

1. Field of the Invention

The present invention relates to a process for the fermentative preparation of D-pantothenic acid and/or its salts or mixtures containing these using microorganisms from the Enterobacteriaceae family, in which at least the glyA gene is enhanced.

2. Description of the Background

Pantothenic acid is produced all over the world in amounts of several thousand tons per year. It is used, inter alia, in human medicine, in the pharmaceutical industry and in the foodstuffs industry. A high proportion of the pantothenic acid produced is used for feeding economically useful animals such as poultry, and pigs. The demand for this material is increasing.

Pantothenic acid can be prepared by chemical synthesis or biotechnically by the fermentation of suitable microorganisms in suitable nutrient media. In the case of chemical synthesis, DL-pantolactone is an important precursor. This is prepared in a multi-step process from formaldehyde, isobutylaldehyde and cyanide, the racemic mixture is resolved in a subsequent process step, D-pantolactone is condensed with β-alanine and D-pantothenic acid is obtained in this way.

The typical commercial form is the calcium salt of D-pantothenic acid. The calcium salt of the racemic mixture D,L-pantothenic acid is also commonly available.

The advantage of fermentative preparation by microorganisms is the direct formation of the desired stereoisomeric form, that is the D-form, which contains no L-pantothenic acid.

Various species of bacteria such as, e.g. *Escherichia coli* (*E. coli*), *Arthrobacter ureafaciens, Corynebacterium erythrogenes, Brevibacterium ammoniagenes* and also yeasts, such as e.g. *Debaromyces castellii* can, as shown in EP-A 0 493 060, produce D-pantothenic acid in a nutrient medium which contains glucose, DL-pantoic acid and β-alanine. Furthermore, EP-A 0 493 060 shows that, in the case of *E. coli*, the formation of D-pantothenic acid is improved by the amplification of pantothenic acid biosynthesis genes from *E. coli* which are contained on the plasmids pFV3 and pFV5, in a nutrient medium which contains glucose, DL-pantoic acid and β-alanine.

EP-A 0 590 857 and U.S. Pat. No. 5,518,906 describe mutants derived from *E. coli* strain IF03547, such as FV5714, FV525, FV814, FV521, FV221, FV6051 and FV5069 which carry resistance to various antimetabolites such as salicylic acid, a-ketobutyric acid, β-hydroxyaspartic acid, O-methylthreonine and a-ketoisovaleric acid. They produce pantoic acid in a nutrient medium which contains glucose, and D-pantothenic acid in a glucose and B-alanine-containing nutrient medium. Furthermore, in EP-A 0 590 857 and U.S. Pat. No. 5,518,906, it is stated that the production of D-pantoic acid is improved in a glucose-containing nutrient media and the production of D-pantothenic acid is improved in a nutrient medium which contains glucose and β-alanine after amplification, in the strains mentioned above, of the pantothenic acid biosynthesis genes panB, panC and panD, which should be present on the plasmid pFV31.

Furthermore, WO 97/10340 reports on the beneficial effect of enhancing the ilvGM operon on the production of D-pantothenic acid. Finally, EP-A-1001027 reports on the effect of enhancing the panE gene on the formation of D-pantothenic acid. According to known procedures, D-pantothenic acid or the corresponding salt is isolated from the fermentation broth and purified (EP-A-0590857 and WO 96/33283) and then used in purified form or the entire D-pantothenic acid-containing broth is dried EP-A-1050219) and used in particular as a foodstuffs additive.

In view of the increasing demand for D-panthothenic acid, there remains a need for new methods of producing this material.

SUMMARY OF THE INVENTION

It is an object of the present invention to provide methods of making D-pantothenic acid and salts thereof, as well as feedstuffs additives containing the same.

The invention provides a process for the preparation of D-pantothenic acid and/or its salts or foodstuffs additives which contain, in addition to these, further constituents from the fermentation by fermentation of microorganisms from the Enterobactericeae family, in particular those which already produce D-pantothenic acid, in which (a) the nucleotide sequence(s) in the microorganisms coding for the endogenous glyA gene is enhanced, in particular overexpressed, under conditions which are suitable for the production of serine hydroxymethyl transferase, (b) D-pantothenic acid and/or its salts are enriched in the medium or in the cells of the microorganisms and (c) the desired products are isolated after completion of fermentation, wherein an amount of $\geq 0$ to 100% of the biomass and/or optionally further constituents of the fermentation broth are separated, wherein the microorganisms produce D-pantothenic acid.

The invention also provides a process in which, after completion of fermentation, all or some of the biomass remains in the fermentation broth and the broth obtained in this way is processed, optionally after being concentrated, to give a solid mixture which contains D-pantothenic acid and/or its salts and which also contains other constituents of the fermentation broth.

Thus, the present invention provides a method of producing D-pantothenic acid and/or a salt thereof, comprising:

fermenting a microorganism of the family Enterobacteriaceae, in which the nucleotide sequence for the endogenous glyA gene is enhanced, in a medium suitable for the production of serine hydroxymethyl transferase, wherein the microorganism produces the D-pantothenic acid and/or a salt thereof.

The present invention also provides a method of producing a feedstuffs additive, comprising:

producing D-pantothenic acid and/or a salt thereof as described above, and combining the D-pantothenic acid and/or a salt thereof with a carrier suitable for use in feedstuffs.

The present invention also provides a vector suitable for expressing the glyA gene from *E. coli* which contains a promoter and the gene sequence.

The present invention also provides a microorganism from the Enterobacteriaceae family, transformed with the vector described above.

The present invention also provides a method for producing D-pantothenic acid and/or a salt thereof by fermenting the microorganism described above.

In particular, yhe present invention also provides a method for producing an animal feedstuffs additive, comprising:
(a) producing D-pantothenic acid or a salt thereof as described above, wherein the alkaline earth metal of the alkaline earth salt is magnesium and/or calcium,
(b) optionally, removing water from the medium,
(c) separating the biomass formed during the fermentation in an amount of 0 to 100%,
(d) optionally, adding one or more magnesium and/or calcium salts of D-pantothenic acid to the fermentation broths from (b), and
(e) producing the feedstuffs additive,
wherein the amount of the added one or more magnesium and/or calcium salts of D-pantothenic acid is such that the amount thereof in the feedstuffs additive is in the range from 1 about 20 to 80 wt. % based on the dry mass of the feedstuffs additive.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

Figure 1:
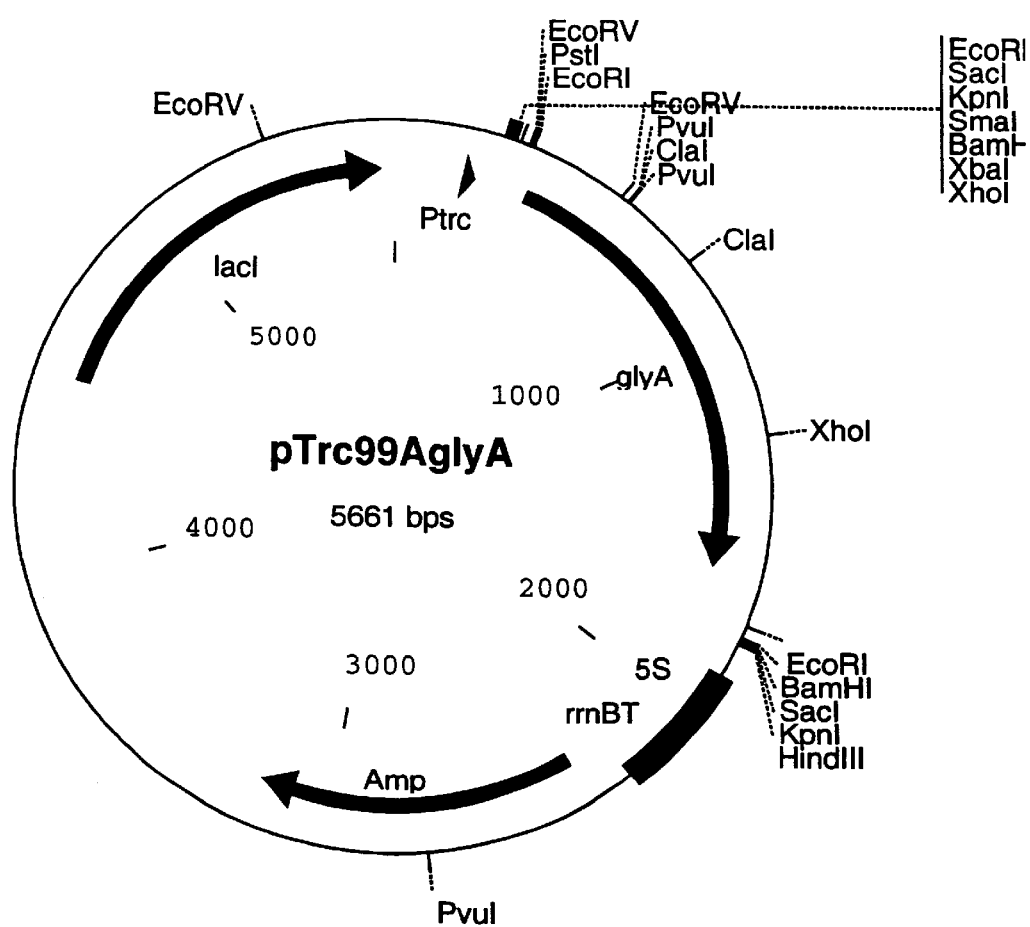
FIG. 1: Map of the plasmid pTrc99AglyA containing the glyA gene.

Data relating to lengths are given as approximate values. The abbreviations and names used are as follows:
Amp: Ampicillin resistance gene
Tc: Tetracyclin resistance gene
lacI: Gene for repressor protein of the trc promoter
Ptrc: trc promoter region, IPTG inducible
glyA: Coding region of the glyA gene
5S: 5S rRNA region
rrnBT: rRNA terminator region
panB: Coding region of the panB gene
panC: Coding region of the panC gene
The abbreviations for the restriction enzymes are as follows:
BamHI: Restriction endonuclease from *Bacillus amyloliquefaciens*
BglII: Restriction endonuclease from *Bacillus globigii*
ClaI: Restriction endonuclease from *Caryphanon latum*
EcoRI: Restriction endonuclease from *Escherichia coli*
EcoRV: Restriction endonuclease from *Escherichia coli*
HindIII: Restriction endonuclease from *Haemophilus influenzae*
KpnI: Restriction endonuclease from *Klebsiella pneumoniae*
PstI: Restriction endonuclease from *Providencia stuartii*
PvuI: Restriction endonuclease from *Proteus vulgaris*
SacI: Restriction endonuclease from *Streptomyces achromogenes*
SalI: Restriction endonuclease from *Streptomyces albus*
SmaI: Restriction endonuclease from *Serratia marcescens*
XbaI: Restriction endonuclease from *Xanthomonas badrii*
XhoI: Restriction endonuclease from *Xanthomonas holcicola*.

DETAILED DESCRIPTION OF THE INVENTION

Whenever D-pantothenic acid, pantothenic acid or pantothenate are mentioned in the following, these are intended to mean not only the free acids but also the salts of D-pantothenic acid such as e.g. the calcium, sodium, ammonium or potassium salt.

In this connection, the expression "enhancement" describes the increase in cellular activity of one or more enzymes or proteins in a microorganism which are coded by the corresponding DNA by, for example, increasing the copy number of the gene or genes, using a strong promoter or a gene or allele which codes for a corresponding enzyme or protein with high activity and optionally combining these steps.

As a result of the enhancement step, in particular overexpression, the activity or concentration of the corresponding protein is generally increased by at least 10%, 25%, 50%, 75%, 100%, 150%, 200%, 300%, 400% or 500%, at most up to 1000% or 2000%, with respect to that of the wild type protein or the protein in the initial microorganism.

Microorganisms which are provided by the present invention can produce D-pantothenic acid from glucose, saccharose, lactose, fructose, maltose, molasses, starch, cellulose or from glycerine and ethanol. They are members of the Enterobacteriaceae family, in particular from the genus Escherichia. From the genus Escherichia, the species *Escherichia coli* is mentioned in particular. Within the species *Escherichia coli*, the so-called K-12 strains such as e.g. the strain MG1655 or W3110 (Neidhard et al.: *Escherichia coli* and Salmonella. Cellular and Molecular Biology (ASM Press, Washington D.C.)) or the *Escherichia coli* wild type strain IF03547 (Institut für Fermentation, Osaka, Japan) and mutants derived therefrom are suitable, these having the ability to produce D-pantothenic acid.

Suitable D-pantothenic acid-producing strains from the genus Escherichia, in particular from the species *Escherichia coli* are for example
*Escherichia coli* FV5069/pFV31
*Escherichia coli* FV5069/pFV202
*Escherichia coli* FE6/pFE80 and
*Escherichia coli* KE3.

It was found that Enterobacteriaceae, after overexpression of the glyA gene coding for serine hydroxymethyl transferase produce D-pantothenic acid in an improved way.

The nucleotide sequences in the glyA gene from *Escherichia coli* were published by Plamann et al (Nucleic Acids Research 11(7):2065–2075(1983)) and can also be obtained from the genome sequence for *Escherichia coli*, under Accession Number AE000374, published by Blattner et al. (Science 277, 1453–1462 (1997).

The glyA gene described in the literature references cited above can be used in accordance with the invention. Furthermore, alleles of the glyA gene which are produced by degeneracy of the genetic code or by functionally neutral sense mutations may be used.

In order to produce an overexpression, the copy number of the corresponding genes can be increased or the promoter and regulation region or the ribosome bonding site which is located upstream of the structure gene can be mutated. Expression cassettes which are incorporated upstream of the structure gene act in the same way. It is also possible to increase expression during the course of fermentative D-pantothenic acid production by means of inducible promoters. Expression is also improved by steps to extend the lifetime of m-RNA. Furthermore, by inhibiting degradation of the enzyme protein, enzyme activity is also enhanced. The genes or gene structures may either be present in plasmids with different copy numbers or integrated and amplified in the chromosome. Alternatively, overexpression of the genes involved can be achieved by changing the composition of the medium and by culture management.

One skilled in the art will find instructions for this, inter alia, in Chang and Cohen (Journal of Bacteriology 134:1141–1156 (1978)), in Hartley and Gregori (Gene 13:347–353 (1981)), in Amann and Brosius (Gene 40:183–190 (1985)), in de Broer et al. (Proceedings of the National of Sciences of the United States of America 80:21–25 (1983)), in LaVallie et al. (BIO/TECHNOLOGY 11, 187–193 (1993)), in PCT/US97/13359, in Llosa et al. (Plasmid 26:222–224 (1991)), in Quandt and Klipp (Gene 80:161–169 (1989)), in Hamilton (Journal of Bacteriology 171:4617–4622 (1989), in Jensen and Hammer (Biotechnology and Bioengineering 58, 191–195 (1998) and in well-known textbooks on genetics and molecular biology.

Plasmid vectors which are replicable in Enterobacteriaceae such as e.g. cloning vectors derived from pACYC184 (Bartolomé et al.; Gene 102, 75–78 (1991)), pTrc99A (Amann et al.; Gene 69:301–315 (1988)) or pSC 101 derivatives (Vocke and Bastia, Proceedings of the National Academy of Science USA 80 (21):6557–6561 (1983)) can be used. In one process according to the invention, a strain transformed with a plasmid vector can be used, wherein the plasmid vector contains at least the nucleotide sequence coding for the glyA gene.

Furthermore, it may be advantageous for the production of D-pantothenic acid using strains from the Enterobacteriaceae family, in addition to enhancing the glyA gene, to enhance, in particular to overexpress, separately or together one or more endogenous genes selected from the group the ilvGM operon coding for acetohydroxy acid synthase II (WO 97/10340)

the panB gene coding for ketopantoate-hydroxymethyl transferase (U.S. Pat. No. 5,518,906), the panE gene coding for ketopantoate reductase (EP-A-1001027)

the panD gene coding for aspartate decarboxylase (U.S. Pat. No. 5,518,906), the panC gene coding for pantothenate synthetase (U.S. Pat. No. 5,518,906), the serC gene coding for phosphoserine transaminase (Duncan und Coggins, Biochemical Journal 234:49–57 (1986)) and the gcvT, gcvH and gcvP genes coding for the glycine cleavage system (Okamura-Ikeda et al., European Journal of Biochemistry 216, 539–548 (1993)).

Finally, it may be advantageous for the production of D-pantothenic acid using strains of the Enterobacteriaceae family, in addition to enhancing the glyA gene, to attenuate, in particular to switch off or express at a lower level the following gene, the avtA gene coding for transaminase C (EP-A-1001027).

The expression "attenuation" in this connection describes the reduction in, or switching off, of the intracellular activity of one or more enzymes (proteins) in a microorganism which are coded by the corresponding DNA by, for example, using a weak promoter or using a gene or allele which codes for a corresponding enzyme (protein) with a lower activity or inactivates the corresponding gene or enzyme (protein) and optionally combining these steps.

The activity or concentration of the corresponding protein is generally lowered to 0 to 75%, 0 to 50%, 0 to 25%, 0 to 10% or 0 to 5% of the activity or concentration of the wild type protein or of the activity or concentration of the protein in the initial microorganism by the attenuation step.

Furthermore, it may be advantageous for the production of D-pantothenic acid, in addition to overexpressing the glyA gene, to switch off undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982). In the process according to the invention, bacteria may be used in which the metabolic pathways which reduce the formation of D-pantothenic acid are at least partially switched off.

Microorganisms prepared according to the invention can be cultivated in a batch process, in a fed batch process or in a repeated fed batch process. Summaries of known cultivation methods are described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used has to satisfy the requirements of the particular strain in an appropriate manner. Descriptions of culture media for various microorganisms are given in the manual "Manual of Methods for General Bacteriology" by the American Society for Bacteriology (Washington D.C., USA, 1981). Sources of carbon which are used are sugar and carbohydrates such as e.g. glucose, saccharose, lactose, fructose, maltose, molasses, starch and cellulose, oils and fats such as e.g. soy oil, sunflower oil, groundnut oil and coconut butter, fatty acids such as e.g. palmitic acid, stearic acid and linoleic acid, alcohols such as e.g. glycerine and ethanol and organic acids such as e.g. acetic acid. These substances may be used individually or as a mixture.

Sources of nitrogen which are used may be organic nitrogen-containing compounds such as peptones, yeast extract, meat extract, malt extract, maize steep liquor, soy bean flour and urea or inorganic compounds such as ammonium sulfate, ammonium chloride, ammonium phosphate, ammonium carbonate and ammonium nitrate. The sources of nitrogen may be used individually or as a mixture.

Sources of phosphorus which may be used are phosphoric acid, potassium dihydrogen phosphate or dipotassium hydrogen phosphate or the corresponding sodium-containing salts. Furthermore, the culture medium must contain salts of metals, such as e.g. magnesium sulfate or iron sulfate, which are required for growth. Finally, essential growth substances such as amino acids and vitamins can be used in addition to the substances mentioned above. Moreover, precursors of D-pantothenic acid such as aspartate, b-alanine, ketoisovalerate, ketopantoic acid or pantoic acid and optionally their salts can be added to the culture medium. The feedstocks mentioned can be added to the culture in the form of a one-off batch or be fed to the culture medium in an appropriate manner during cultivation.

Basic compounds such as sodium hydroxide, potassium hydroxide, ammonia or ammoniacal water or acid compounds such as phosphoric acid or sulfuric acid are used in a suitable way to control the pH of the culture.

It is also possible, to prepare the alkaline earth salts of pantothenic acid, in particular the calcium salt, to add a suspension or solution of an alkaline earth-containing inorganic compound, such as for example calcium hydroxide, or an organic compound such as the alkaline earth salt of an organic acid, for example calcium acetate, continuously or batchwise during fermentation. The cation required to prepare the desired alkaline earth salt of D-pantothenic acid is introduced directly into the fermentation broth in the desired amount in this way, generally in the ratio of 0.8 to 1.2 to 1, with respect to the pantothenic acid, preferably in stoichiometric amounts.

Atifoaming agents such as e.g. polyglycol esters of fatty acids are used to regulate the production of foam. To maintain the stability of plasmids, suitable selectively acting substances, e.g. antibiotics, may be added to the medium. In order to maintain the presence of aerobic conditions, oxygen or oxygen-containing gas mixtures such as e.g. air are introduced into the culture. The temperature of the culture is usually 25° C. to 45° C. and preferably 30° C. to 40° C. The culture is continued until a maximum of D-pantothenic has formed. This objective is usually achieved within 10 hours to 160 hours.

The D-pantothenic acid or the corresponding salts of D-pantothenic acid contained in the fermentation broth may then be isolated and purified using known procedures. It is also possible preferably first to partly ($^3$0 to 100%) or completely remove the biomass from the fermentation broth containing D-pantothenic acid and/or its salts by known methods of separation such as, for example, centrifuging, filtering, decanting or a combination of these. However, it is also possible to leave all of the biomass in the fermentation broth. In general, the suspension or solution is preferably concentrated and worked up to produce a powder, for example using a spray dryer or a freeze drying unit. Then this powder is converted into a coarse-grained, very free-flowing, storable and largely dust-free product with a particle size distribution of 20 to 2000 $\mu$m, in particular 100 to 140 $\mu$m, using suitable compacting or granulating methods, e.g. also pelletizing. The use of conventional organic or inorganic auxiliary substances, or supports such as starch, gelatin, cellulose derivatives or similar substances, such as are conventionally used in foodstuffs or animal feed processing as -binders, gelling agents or thickeners, or other substances such as, for example, silicas, silicates or stearates is advantageous when granulating or compacting.

Alternatively, the fermentation product, with or without other conventional constituents from the fermentation broth, can be deposited onto an organic or inorganic support substance which is known and conventionally used in the foodstuffs processing sector such as, for example, silicas, silicates, grist, bran, flour, starch, sugar or others and/or stabilized with conventional thickeners or binders. Examples of applications and processes for this are described in the literature (Die Mühle+Mischfuttertechnik 132 (1995) 49, page 817).

Optionally, in a suitable process step, D-pantothenic acid or the desired salt of D-pantothenic acid or a preparation containing these compounds is added to the product in order to produce or adjust to the desired concentration of pantothenic acid or the desired salt.

The desired concentration is generally in the range 20 to 80 wt. % (dry weight). This range includes all specific values and subranges therebetween, such as 30, 40, 50, 60, and 70 wt. %.

The concentration of pantothenic acid can be determined using known chemical (Velisek; Chromatographic Science 60, 515–560 (1992)) or microbiological methods such as e.g. the Lactobacillus plantarum test (DIFCO MANUAL, 10th edition, p. 1100–1102; Michigan, USA).

A pure culture of the following microorganism was deposited at the German Collection of Microorganisms and Cell Cultures (DSMZ, Braunschweig, Germany) on 8th September 2000 in accordance with the Budapest treaty:

*Escherichia coli* K12 strain FE6-1, as DSM 13721.

EXAMPLES

Having generally described this invention, a further understanding can be obtained by reference to certain specific examples which are provided herein for purposes of illustration only and are not intended to be limiting unless otherwise specified.

The minimal (M9) and complete (LB) media for *Escherichia coli* are described by J. H. Miller (A short course in bacterial genetics (1992), Cold Spring Harbor Laboratory Press). The isolation of plasmid DNA from *Escherichia coli* and all the techniques for restriction, Klenow and alkaline phosphatase treatment are performed in accordance with Sambrook et al. (Molecular cloning—A laboratory manual (1989) Cold Spring Harbor Laboratory Press). The transformation of *Escherichia coli*, if not described differently, is performed in accordance with Chung et al. (Proceedings of the National Academy of Sciences of the United States of America USA (1989) 86: 2172–2175).

Example 1

Construction of the Expression Plasmid pTrc99AglyA

The glyA gene from *E. coli* K12 is amplified using the polymerase chain reaction (PCR) and synthetic oligonucleotides. Starting from the nucleotide sequence for the glyA gene in *E. coli* K12 MG1655 (Accession Number AE000341, Blattner et al. (Science 277, 1453–1462 (1997),) PCR primers are synthesized (MWG Biotech, Ebersberg, Germany):

glyA1: 5'-GTTAGCTGAGTCAGGAGATG-3'
glyA2: 5'-TACGCTTATCAGGCCTACAC-3'

The chromosomal *E. coli* K12 MG1655 DNA used for the PCR is isolated according to data provided by the manufacturer using "Qiagen Genomic-tips 100/G" (QIAGEN, Hilden, Germany). An approximately 1400 bp size DNA fragment can be amplified with specific primers under standard PCR conditions (Innis et al. (1990) PCR Protocols. A Guide to Methods and Applications, Academic Press) using Pfu DNA polymerase (Promega Corporation, Madison, USA). The PCR product is ligated according to data provided by the manufacturer using the vector pCR-Blunt II-TOPO (Zero Blunt TOPO PCR Cloning Kit, Invitrogen, Groningen, Netherlands) and transformed in *E. coli* strain TOP10. The selection of cells carrying the plasmid is performed on LB agar which has been treated with 50 $\mu$g/ml kanamycin. After isolation of the plasmid DNA, the vector pCR-Blunt II-TOPOglyA is cleaved with restriction enzymes HindIII and XbaI and the glyA fragment is isolated after separation in 0.8% agarose gel using the QIAquick Gel Extraction Kit (QIAGEN, Hilden, Germany). The vector pTrc99A (Pharmacia Biotech, Uppsala, Sweden) is cleaved with the enzymes HindIII and XbaI and ligated with the isolated glyA fragment. *E. coli* strain XL1-Blue MRF' (Stratagene, La Jolla, USA) is transformed with the ligation mixture and cells carrying the plasmid are selected on LB agar which has been treated with 50 $\mu$g/ml ampicillin. Successful cloning can be detected after plasmid DNA isolation by control cleavage with the enzyme SspI. The plasmid is called pTrc99AglyA (FIG. 1).

Example 2

Preparing the Strain FE6-1/pTrc99AglyA

*E. coli* strain FE6 is a valine-resistant mutant of *E. coli* K12 MG1655 (U.S. Pat. No. 6,171,845) and is deposited as DSM12379 at the German Collection of Microorganisms and Cell Cultures (DSMZ, Braunschweig, Germany). Starting from FE6, spontaneous mutants are isolated after incubation at 37° C. on minimal agar which has been treated with 2 g/l glucose and 1 g/l β-hydroxyaspartic acid. A selected β-hydroxyaspartic acid-resistant single colony is then incubated at 37° C. on minimal agar which contains 2 g/l glucose and 0.2 g/l O-methylthreonine. A mutant called FE6-1 is resistant to valine, a-ketoisovaleric acid, β-hydroxyaspartic acid and O-methylthreonine following this step. The plasmid pTrc99AglyA is transformed in strain FE6-1 and cells carrying the plasmid are selected on LB agar which has been treated with 50 μ/ml ampicillin. The strain obtained is called FE6-1/pTrc99AglyA.

Example 3

Preparing the Strain FE6-1/pTrc99AglyA,pACYC 184panBC

Figure 2:
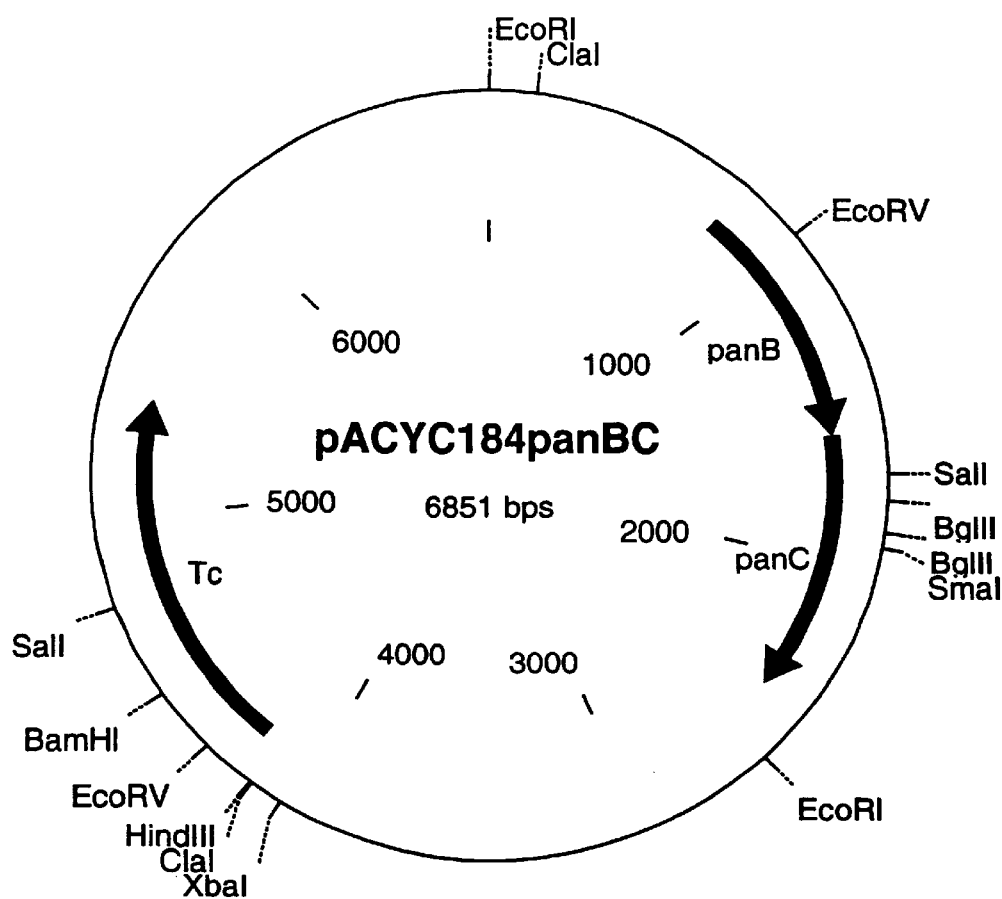
FIG. 2: Map of the plasmid pACYC184panBC containing the panBC gene.

The D-pantothenic acid-producing *E. coli* strain FV5069/pFV31 is described in EP-A-0590857 and is deposited as FERM BP 4395 in accordance with the Budapest treaty. The plasmid pFV31 is isolated from FV5069/pFV31 and cleaved with restriction enzyme EcoRI. After separation in 0.8% agarose gel, the approximately 2600 bp size DNA fragment on which the panBC genes are present is isolated using the QIAquick Gel Extraction Kit (QIAGEN, Hilden, Germany). The vector pACYC184 (Chang, A. C. Y. und Cohen, S. N., Journal of Bacteriology 134, 1141–1156 (1978); ATCC37033 (American Type Culture Collection, Manassas, USA)) is cleaved with the enzyme EcoRI and ligated with the isolated panBC fragment. *E. coli* strain FE6-1 is transformed with the ligation mixture and cells which carry the plasmid are selected on LB agar which has been treated with 10 μg/ml tetracyclin. Successful cloning can be detected by control cleavage with the enzymes EcoRV and EcoRI after plasmid DNA isolation. The plasmid is called pACYC184panBC (FIG. 2). The strain FE6-1/pTrc99AglyA described in example 2 is transformed with the plasmid pACYC184panBC. Selection is performed on LB agar which has been treated with 50 μg/ml ampicillin and 10 μg/ml tetracyclin. The strain produced in this way is called FE6-1/pTrc99AglyA, pACYC184panBC.

Example 4

Production of D-Pantothenic Acid with Strains Derived from FE6-1

Pantothenate production by *E. coli* strains FE6-1, FE6-1/pTrc99AglyA, FE6-1/pACYC184panBC, FE6-1/pTrc99AglyA, pACYC184panBC is checked in batch cultures of 10 ml which are contained in 100 ml conical flasks. For this, 10 ml of preculture medium with the following composition: 2 g/l yeast extract, 10 g/l $(NH_4)_2SO_4$, 1 g/l KH2PO4, 0.5 g/l $MgSO_4 \cdot 7H_2O$, 15 g/l $CaCO_3$, 20 g/l glucose, is inoculated with a single colony and incubated for 20 hours at 33° C. and 200 rpm in an ESR incubator from Kühner AG (Birsfelden, Switzerland). 200 μl portions of this preculture are each inoculated into 10 ml of production medium (25 g/l $(NH_4)_2SO_4$, 2 g/l $KH_2PO_4$, 1 g/l $MgSO_4 \cdot 7H_2O$, 0.03 g/l $FeSO_4 \cdot 7H_2O$, 0.018 g/l $MnSO_4 \cdot 1H_2O$, 30 g/l $CaCO_3$, 20 g/l glucose, 20 g/l β-alanine, 250 mg/l thiamine) and incubated for 48 hours at 37° C. During the incubation of FE6-1/pTrc99AglyA, 50 mg/l ampicillin are also added to the media, during the incubation of FE6-1/pACYC184panBC, 10 mg/l tetracyclin are also added to the media and during the incubation of FE6-1/pTrc99AglyA,pACYC184panBC, 50 mg/l ampicillin and 10 mg/l tetracyclin are also added to the media. After incubation, the optical density (OD) of the culture suspension is determined at a test wavelength of 660 nm using a LP2W photometer from the Dr. Lange Co. (Düsseldorf, Germany).

Then the concentration of D-pantothenate formed in the sterile filtered culture supernatant liquid is determined using the Lactobacillus plantarum ATCC8014 pantothenate assays in accordance with data from DIFCO (DIFCO MANUAL, 10th Edition, p. 1100–1102; Michigan, USA). The calcium salt of D(+)-pantothenic acid hydrate (catalogue number 25,972-1, Sigma-Aldrich, Deisenhofen, Germany) is used for calibration purposes.

Table 1 gives the results of the test.

TABLE 1

| Strain | OD (660 nm) | Pantothenate mg/l |
| --- | --- | --- |
| FE6-1 | 10.6 | 19 |
| FE6-1/pTrc99AglyA | 9.2 | 39 |
| FE6-1/pACYC184panBC | 8.4 | 540 |
| FE6-1/pTrc99AglyA, pACYC184panBC | 9.4 | 820 |

The publications cited above are incorporated herein by reference.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 101 06 461.6, filed on Feb. 13, 2001, which is incorporated herein by reference.

What is claimed is:

1. A method of producing D-pantothenic acid and/or a salt thereof, comprising:
    fermenting a microorganism of the family Enterobacteriaceae, in which the nucleotide sequence for the endogenous glyA gene is overexpressed in a medium suitable for the production of serine hydroxymethyl transferase, wherein the microorganism is *Escherichia coli* and produces the D-pantothenic acid and/or a salt thereof.

2. The method of claim 1, wherein the medium is enriched in the D-pantothenic acid and/or a salt thereof and/or the cells of the microorganism are enriched in the D-pantothenic acid and/or a salt thereof.

3. The method of claim 1, further comprising isolating at least a portion of the D-pantothenic acid and/or a salt thereof from the medium.

4. The method of claim 1, further comprising isolating at least a portion of the biomass from the medium.

5. The method of claim 1, wherein the fermentation is performed in the presence of at least one alkaline earth salt, which is supplied continuously or batchwise to the medium, and a product containing an alkaline earth salt of D-pantothenic acid is produced.

6. The method of claim 1, wherein one or more of the endogenous genes selected from the group consisting of
    the ilvGM operon coding for acetohydroxy acid synthase II,
    the panB gene coding for ketopantoate hydroxymethyl transferase, the panE gene coding for ketopantoate reductase, the panD gene coding for aspartate decarboxylase, and the panC gene coding for pantothenate synthetase are overexpressed in the microorganism.

7. The method of claim 1, wherein the activity or concentration of the glyA gene product is increased by 10 to 2000%, with respect to that of the protein in the initial microogranism.

8. The method of claim 1, wherein transformed strains are used in which the glyA gene is present in plasmids or is integrated into the chromosome.

9. A method for producing D-pantothenic acid and/or a salt thereof by fermenting a transformed microorganism wherein the microorganism is *Escherichia coli* transformed with a vector containing a promotor operably linked to the *Escherichia coli* glyA gene.

10. A method for producing D-pantothenic acid and/or a salt thereof by fermenting a transformed microorganism wherein the microorganism is *Escherichia coli* transformed with pTrc99AglyA.

* * * * *